(12) United States Patent
Lee (10) Patent No.: US 11,464,315 B2
(45) Date of Patent: Oct. 11, 2022

(54) DROPPING PIPETTE-TYPE COSMETIC CONTAINER COMPRISING PRESSING BUTTON HAVING ADJUSTABLE DESCENDING DISTANCE

(71) Applicant: PUM-TECH KOREA CO., LTD, Incheon (KR)

(72) Inventor: Do Hoon Lee, Incheon (KR)

(73) Assignee: PUM-TECH KOREA CO., LTD, Incheon (KR)

( * ) Notice: Subject to any disclaimer, the term of this patent is extended or adjusted under 35 U.S.C. 154(b) by 133 days.

(21) Appl. No.: 16/969,171

(22) PCT Filed: Jan. 8, 2019

(86) PCT No.: PCT/KR2019/000282
§ 371 (c)(1),
(2) Date: Aug. 11, 2020

(87) PCT Pub. No.: WO2019/160244
PCT Pub. Date: Aug. 22, 2019

(65) Prior Publication Data
US 2020/0397116 A1    Dec. 24, 2020

(30) Foreign Application Priority Data

Feb. 14, 2018 (KR) .......................... 10-2018-0018212

(51) Int. Cl.
*B43K 1/06* (2006.01)
*A45D 34/04* (2006.01)
(Continued)

(52) U.S. Cl.
CPC ............... *A45D 34/04* (2013.01); *B65D 1/08* (2013.01); *B65D 81/3255* (2013.01)

(58) Field of Classification Search
CPC ........ A45D 34/04; A45D 34/045; B65D 1/08; B65D 81/3255
(Continued)

(56) References Cited

U.S. PATENT DOCUMENTS 9,237,793 B2 * 1/2016 Choi .................... B05B 11/3007
9,546,026 B2 * 1/2017 Drugeon ............... B01L 3/0282
(Continued)

FOREIGN PATENT DOCUMENTS

JP      10059428 A    3/1998
KR    200484156 Y1   8/2007
(Continued)

*Primary Examiner* — Jennifer C Chiang
(74) *Attorney, Agent, or Firm* — Heedong Chae; Lucem, PC (57) ABSTRACT

A dropping pipette-type cosmetic container includes a container body having a discharge port formed on one side thereof, a downward movement limiting member coupled to the other side of the container body, a pressing button rotatably coupled to the downward movement limiting member and configured to move downward by pressurization, and an elastic member for elastically supporting the pressing button; the downward movement limiting member has multiple main grooves formed thereon at different depths and has auxiliary grooves formed thereon so as to have the same depths as those of respective main grooves, which have different depths, and to constitute pairs therewith; main protrusions to be inserted into the main grooves and auxiliary protrusions to be inserted into the auxiliary grooves are formed on the pressing button so as to correspond to each other.

10 Claims, 11 Drawing Sheets

(51) Int. Cl.
*B65D 1/08* (2006.01)
*B65D 81/32* (2006.01)

(58) Field of Classification Search
USPC .................................................. 401/265, 273
See application file for complete search history.

(56) References Cited

U.S. PATENT DOCUMENTS

| | | | | |
|---|---|---|---|---|
| 10,278,474 B2* | 5/2019 | Moon | .................... | A45D 34/04 |
| 2020/0154851 A1* | 5/2020 | Jacob | .................... | B65D 25/08 |

FOREIGN PATENT DOCUMENTS

| | | | | |
|---|---|---|---|---|
| KR | 1020120054716 A | | 5/2012 | |
| KR | 101242201 B1 | | 3/2013 | |
| KR | 1020150087110 A | | 7/2015 | |
| WO | WO-2014086719 A1 * | | 6/2014 | ............. A45D 34/00 |

* cited by examiner

DROPPING PIPETTE-TYPE COSMETIC CONTAINER COMPRISING PRESSING BUTTON HAVING ADJUSTABLE DESCENDING DISTANCE

BACKGROUND

The present invention relates to a dropping pipette-type cosmetic container comprising a pressing button having an adjustable descending distance. More specifically, the present invention relates to a dropping pipette-type cosmetic container including a pressing button having an adjustable descending distance, wherein the cosmetic container includes a container body having a discharge port formed on one side thereof, a downward movement limiting member coupled to the other side of the container body, a pressing button rotatably coupled to the downward movement limiting member and configured to move downward by means of pressurization, and an elastic member for elastically supporting the pressing button, wherein the downward movement limiting member has multiple main grooves formed thereon at different depths and has auxiliary grooves formed thereon so as to have the same depths as those of respective main grooves, which have different depths, and to constitute pairs therewith; main protrusions to be inserted into the main grooves and auxiliary protrusions to be inserted into the auxiliary grooves are formed on the pressing button so as to correspond to each other; if the pressing button is rotated by a predetermined angle and then pressurized, the main protrusions of the pressing button descend from the main grooves of the downward movement limiting member, and the auxiliary protrusions are simultaneously inserted into the auxiliary grooves; and the pressing button accordingly descends stably while maintaining a balance without tilting toward any side.

In general, women use various cosmetics to make their appearance more beautiful. The cosmetics are classified into basic cosmetics, color cosmetics, and functional cosmetics according to the purpose of use.

As the cosmetics described above have been developed, there is a need to develop various cosmetic containers capable of containing cosmetics.

Among cosmetics, liquid or gel-type cosmetics having a viscosity are generally stored in a cosmetic container such as a tube container, a rigid plastic container, or a glass container. When applying makeup, the cosmetic container is pressurized or turned over to discharge the cosmetics into the user's hand, and then, the cosmetics are applied to the skin by using a cosmetic tool such as a puff or the user's hands.

However, as described above, according to the conventional cosmetic container, it is difficult to constantly adjust the amount of cosmetics to be discharged every time, thereby causing waste of cosmetics.

Figure 1:
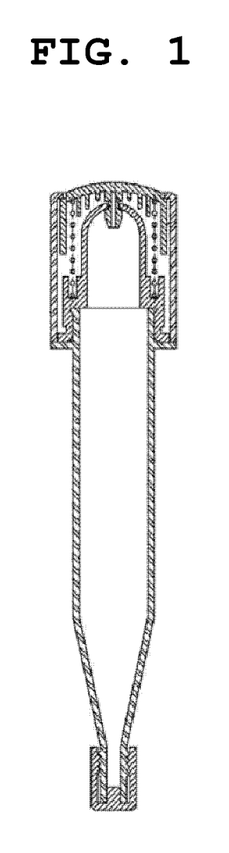
FIG. 1 is a view showing a dropper-type cosmetic container capable of quantitative dispensing according to the related art.

To solve the problems described above, as shown in FIG. 1, there has been disclosed a dropping pipette-type cosmetic container capable of quantitative dispensing in Korean Registered Utility Model No. 20-0440620. The dropping pipette-type cosmetic container according to the related art includes a pipette-type body having a discharge port at a lower end thereof, where an opening and closing cap is coupled to the discharge port, a soft elastic inner cap is coupled to an upper portion of the pipette-type body, an outer cap covers and is fixed to an upper side of the elastic inner cap, and a push button is formed in the outer cap such that contents in the pipette-type body are discharged through the discharge port by pressing the push button.

However, in the conventional dropping pipette-type cosmetic container, the user cannot adjust the descending distance of the push button according to the makeup portion and method.

To solve the problems described above, as shown in FIG. 2, there has been disclosed a dropping pipette-type cosmetic container having a quantitative extraction function in Korean Registered Utility Model No. 20-0484156. According to the related art, a pressure limiting protrusion 1a is formed on an outer periphery of a push button 1, and a pressure limiting groove 2a is formed on one side of a rotating body 2 with a plurality of sills step by step, such that the pressure limiting projection 1a of the push button 1 is inserted into the pressure limiting groove 2a. Accordingly, as the rotating body 2 is rotated, the distance at which the push button 1 is pressed may be adjusted step by step, and thus, a desired amount of cosmetic liquid may be taken out.

Figure 2:
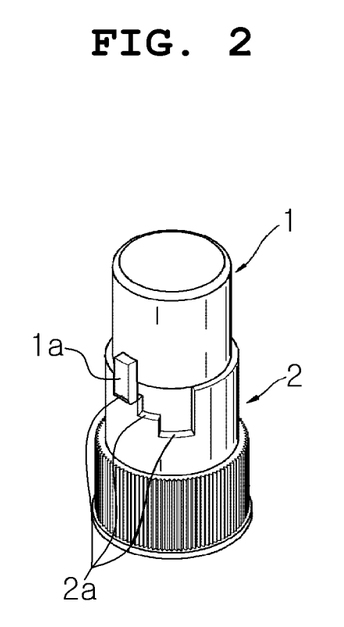
FIG. 2 is a view showing a dropper-type cosmetic container having a quantitative dispensing function according to the related art.

However, according to the related art, since the pressure limiting protrusion 1a is formed only on one side of the push button 1, when the push button 1 is pressed, the push button 1 cannot be stably moved while maintaining a horizontal level and tilts to one side, thereby causing an erroneous operation.

In addition, according to the related art, after the user rotates the rotating body 2 at a certain angle in order to adjust the amount of the cosmetic liquid taken out, when the push button 1 is pressed to allow the pressure limiting protrusion 1a of the push button 1 to move down in the pressure limiting groove 2a of the rotating body 2, the pressure limiting protrusion 1a of the push button 1 is latched to another adjacent sill while moving around, so that the push button 1 is not pressed. In addition, it is difficult to control the amount of the cosmetic liquid taken out because it is not confirmed which sill of the pressure limiting protrusion 1a is located in the pressure limiting groove 2a.

SUMMARY

To solve the problems described above, an object of the present invention is to provide a dropping pipette-type cosmetic container comprising a pressing button having an adjustable descending distance, wherein the cosmetic container comprises a container body having a discharge port formed on one side thereof, a downward movement limiting member coupled to the other side of the container body, a pressing button rotatably coupled to the downward movement limiting member and configured to move downward by means of pressurization, and an elastic member for elastically supporting the pressing button, wherein the downward movement limiting member has multiple main grooves formed thereon at different depths and has auxiliary grooves formed thereon so as to have the same depths as those of respective main grooves, which have different depths, and to constitute pairs therewith; main protrusions to be inserted into the main grooves and auxiliary protrusions to be inserted into the auxiliary grooves are formed on the pressing button so as to correspond to each other; if the pressing button is rotated by a predetermined angle and then pressurized, the main protrusions of the pressing button descend from the main grooves of the downward movement limiting member, and the auxiliary protrusions are simultaneously inserted into the auxiliary grooves; and the pressing button accordingly descends stably while maintaining a balance without tilting toward any side.

Another object of the present invention is to provide a dropping pipette-type cosmetic container comprising a pressing button having an adjustable descending distance, wherein elastic slits are formed on both sides of a main protrusion of the pressing button, and the main protrusion protrudes outward so that the main protrusion is maintained to be always inserted into the main groove of a descent limiting member. In addition, when the pressing button is forcibly rotated, the main protrusion of the pressing button is retracted elastically by an elastic slit, exits the main groove, rotates, and is resiliently inserted into another adjacent main groove to prevent the pressing button from being rotated arbitrarily. Therefore, it is possible to prevent the main protrusion of the pressing button from malfunctioning because the main protrusion is caught in another adjacent portion due to the flowing of the main protrusion. In addition, the user may easily recognize through the touch that the lifting distance of the push button is adjusted.

According to the present invention, there is provided a dropping pipette-type cosmetic container including a pressing button having an adjustable descending distance, which includes a container body having a discharge port formed on one side thereof;

a descent limiting member fixedly coupled to an opposite side of the container body, formed with a plurality of main grooves having different depths, and formed with a plurality of auxiliary grooves, which have a same depth as each of the plurality of main grooves and are formed on a descent limiting sill;

a pressing button rotatably coupled to the descent limiting member and having a main protrusion inserted into the main groove and an auxiliary protrusion inserted into the auxiliary groove; and an elastic member for elastically supporting the pressing button, wherein, when the pressing button is rotated at a predetermined angle, the main protrusion of the pressing button is inserted into one of the plurality of main grooves of the descent limiting member while the auxiliary protrusion is located on the auxiliary groove or the descent limiting sill.

The dropping pipette-type cosmetic container may further include a container cover coupled to one side of the container body to open and close a discharge port of the container body.

The dropping pipette-type cosmetic container may further include an outer cap coupled to an opposite side of the container body to surround the container body and the descent limiting member.

The descent limiting member may be formed with a piston insertion hole, and the pressing button is formed with a piston inserted into the piston insertion hole.

The main groove of the descent limiting member may include first to third main grooves having depths different from each other, and the auxiliary groove may include a second auxiliary groove mating with the second main groove and a third auxiliary groove mating with the third main groove.

Preferably, the depth may gradually increase from the first main groove to the second main groove and the third main groove.

The dropping pipette-type cosmetic container may further include elastic slits formed on two sides of the main protrusion of the pressing button, wherein the main protrusion protrudes outward and is kept in an insertion state into the main groove of the descent limiting member such that the main protrusion is elastically inserted into and released from the main groove.

Preferably, an outer diameter of the main protrusion may be larger than an inner diameter of a second upper extension protrusion wheel in which the main groove is formed, and an outer diameter of the auxiliary protrusion may be smaller than the inner diameter of the second upper extension protrusion wheel.

A heterogeneous content containing space may be formed at one side of the descent limiting member to contain a content different from a content contained in the container body, and a heterogeneous content closing part for closing the heterogeneous content containing space may be coupled to the descent limiting member.

The heterogeneous content closing part may be separated from the descent limiting member while being moved by pressing of the pressing button, such that the heterogeneous content containing space is opened to mix heterogeneous contents.

According to the dropping pipette-type cosmetic container comprising a pressing button having an adjustable descending distance of the present invention, the cosmetic container comprises a container body having a discharge port formed on one side thereof, a downward movement limiting member coupled to the other side of the container body, a pressing button rotatably coupled to the downward movement limiting member and configured to move downward by means of pressurization, and an elastic member for elastically supporting the pressing button; the downward movement limiting member has multiple main grooves formed thereon at different depths and has auxiliary grooves formed thereon so as to have the same depths as those of respective main grooves, which have different depths, and to constitute pairs therewith; main protrusions to be inserted into the main grooves and auxiliary protrusions to be inserted into the auxiliary grooves are formed on the pressing button so as to correspond to each other; if the pressing button is rotated by a predetermined angle and then pressurized, the main protrusions of the pressing button descend from the main grooves of the downward movement limiting member, and the auxiliary protrusions are simultaneously inserted into the auxiliary grooves; and the pressing button accordingly descends stably while maintaining a balance without tilting toward any side, so that convenience in use is improved.

In addition, according to the dropping pipette-type cosmetic container comprising a pressing button having an adjustable descending distance of the present invention, cosmetic container comprising a pressing button having an adjustable descending distance, the elastic slits are formed on both sides of a main protrusion of the pressing button, and the main protrusion protrudes outward so that the main protrusion is maintained to be always inserted into the main groove of a descent limiting member. When the pressing button is forcibly rotated, the main protrusion of the pressing button is retracted elastically by an elastic slit, exits the main groove, rotates, and is resiliently inserted into another adjacent main groove to prevent the pressing button from being rotated arbitrarily. Therefore, it is possible to prevent the main protrusion of the pressing button from malfunctioning because the main protrusion is caught in another adjacent portion due to the flowing of the main protrusion. In addition, the user may easily recognize through the touch that the lifting distance of the push button is adjusted.

DETAILED DESCRIPTION OF THE EMBODIMENTS

Technical objects to be achieved by the present invention and embodiments of the present invention will be apparent through preferable embodiments to be described below. Hereinafter, a dropping pipette-type cosmetic container comprising a pressing button having an adjustable descending distance according to the present invention will be described with reference to accompanying drawings.

Figure 3:
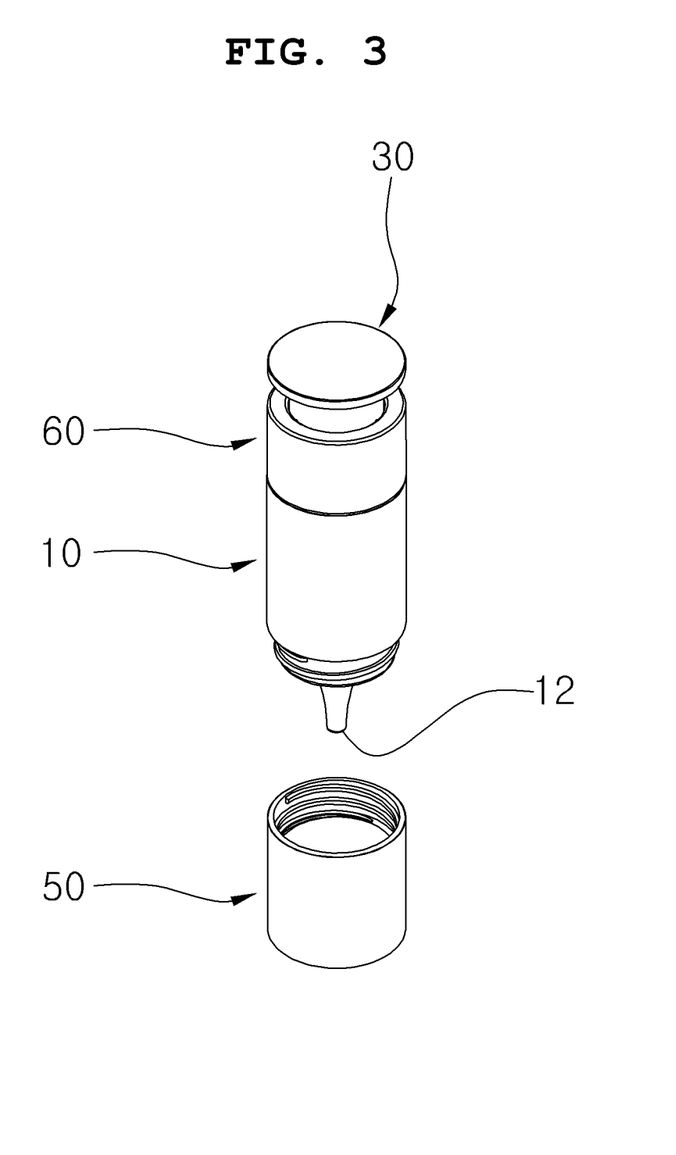
FIG. 3 is a perspective view showing a dropping pipette-type cosmetic container according to an embodiment of the present invention.
Figure 4:
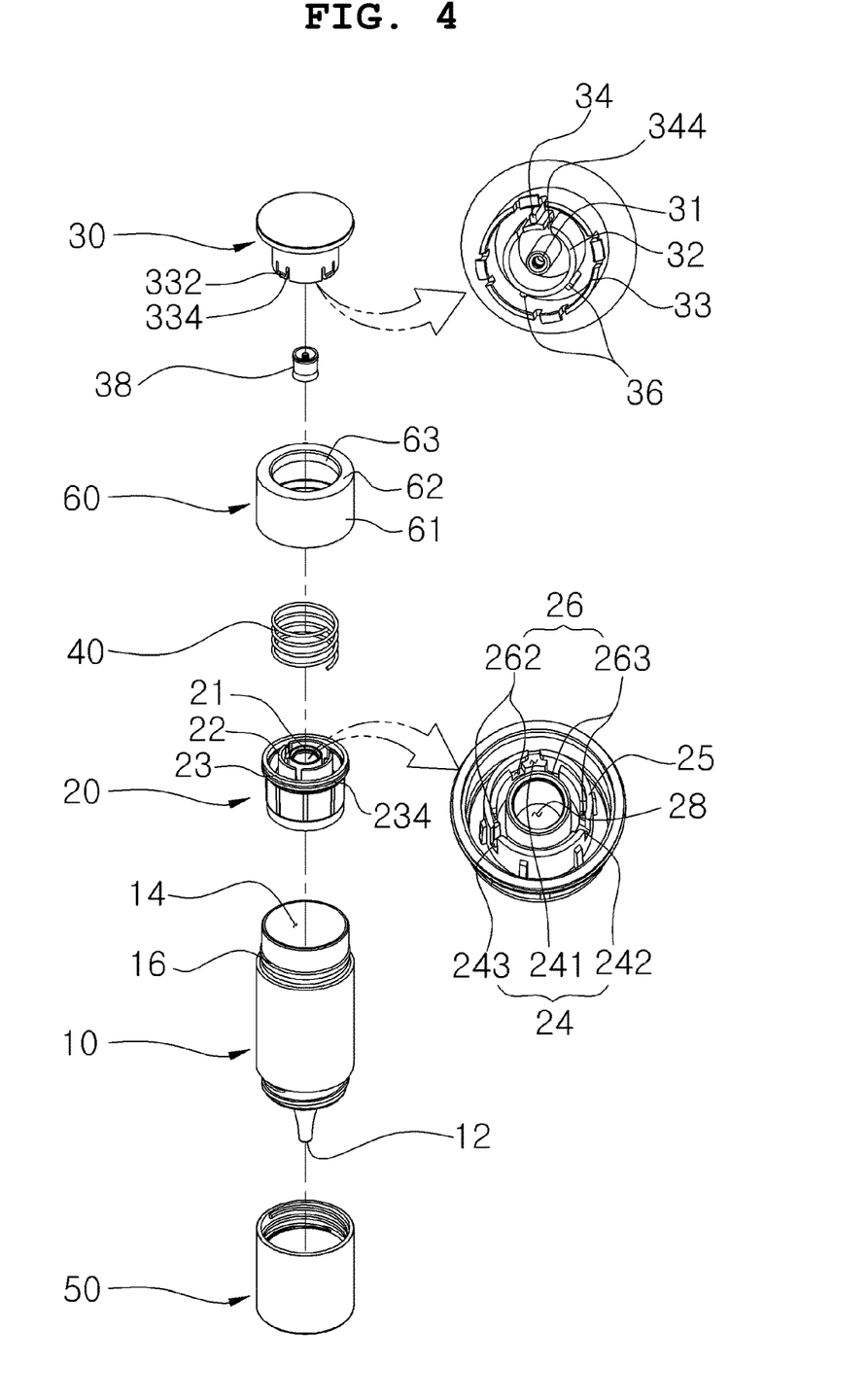
FIG. 4 is an exploded perspective view of a dropping pipette-type cosmetic container according to an embodiment of the present invention.
Figure 5:
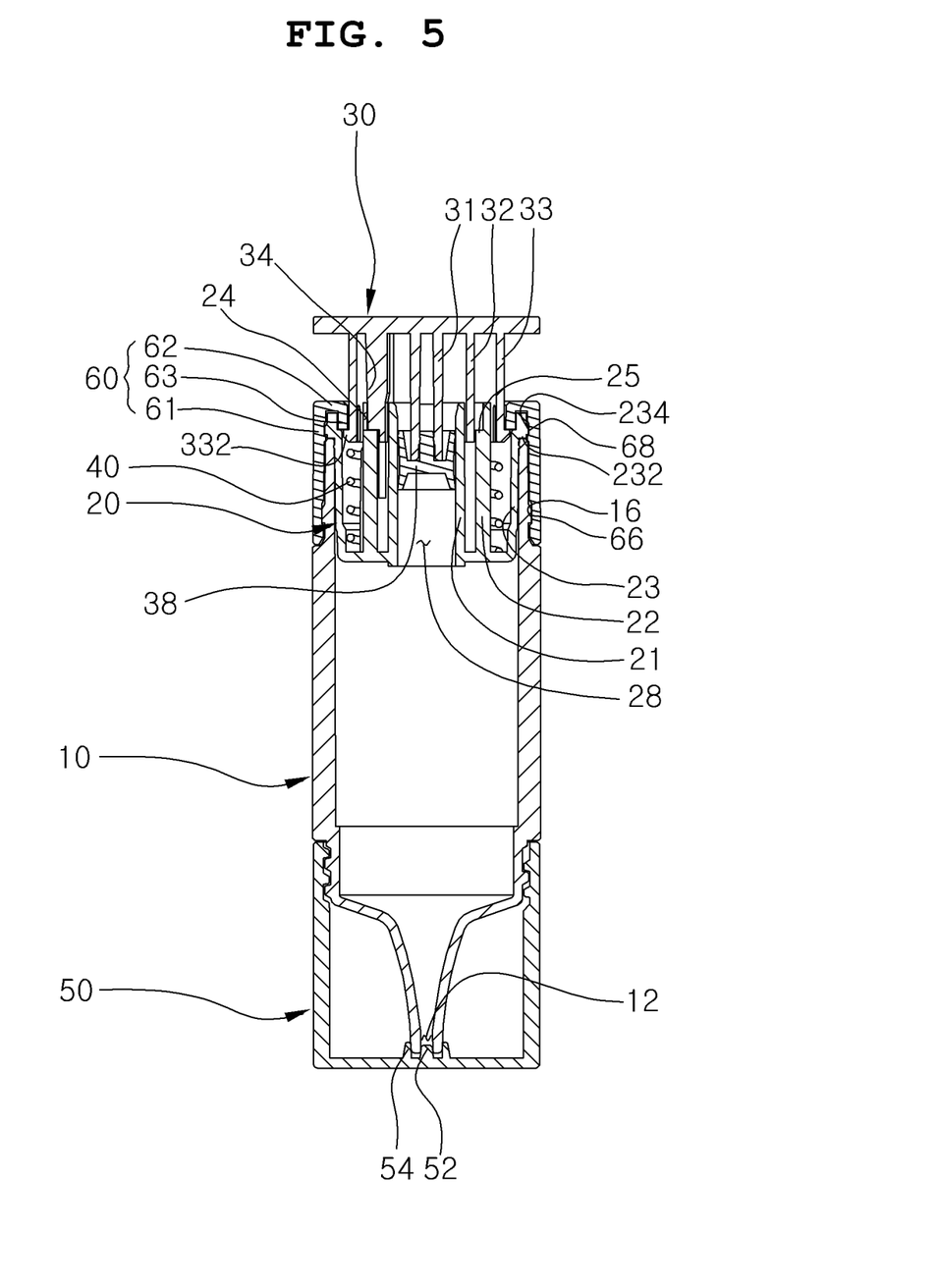
FIG. 5 is a cross-sectional view of a dropping pipette-type cosmetic container according to an embodiment of the present invention.

FIG. 3 is a perspective view showing a dropping pipette-type cosmetic container according to an embodiment of the present invention. FIG. 4 is an exploded perspective view of a dropping pipette-type cosmetic container according to an embodiment of the present invention. FIG. 5 is a cross-sectional view of a dropping pipette-type cosmetic container according to an embodiment of the present invention.

A dropping pipette-type cosmetic container including a pressing button having an adjustable descending distance according to an embodiment of the present invention includes a container body 10 having a discharge port 12 formed on one side thereof; a descent limiting member 20 fixedly coupled to an opposite side of the container body 10, formed with a plurality of main grooves 24 having different depths, and formed on a descent limiting sill 25 with a plurality of auxiliary grooves 26 having the same depth as each of the plurality of main grooves 24; a pressing button 30 rotatably coupled to the descent limiting member 20 and having a main protrusion 34 inserted into the main groove 24 and an auxiliary protrusion 36 inserted into the auxiliary groove 26; and an elastic member 40 for elastically supporting the pressing button 30, where, when the pressing button 30 is rotated at a predetermined angle, the main protrusion 34 of the pressing button 30 is inserted into one of the plurality of main grooves 24 of the descent limiting member 25 while the auxiliary protrusion 36 is located on the auxiliary groove 26 or the descent limiting sill 25.

The container body 10 contains a gel or liquid-type content therein.

As shown in FIG. 4, the container body 10 is formed at one side thereof with a discharge port 12 for discharging contents to an outside and at an opposite side thereof with an opening hole 14.

A screw thread is formed adjacent to the discharge port 12 of the container body 10, and a first coupling protrusion wheel 16 is formed adjacent to the opening hole 14.

A container cover 50 for opening and closing the discharge port 12 of the container body 10 is further coupled to one side of the container body 10.

As shown in FIG. 5, a screw thread is formed on an upper inner periphery of the container cover 50 and coupled to the screw thread of the container body 10.

A sealing protrusion 52 is formed on an inner lower surface of the container cover 50, and a sealing protrusion wheel 54 is formed on an outer side of the sealing protrusion 52. When the container body 10 and the container cover 50 are coupled to each other, the sealing protrusion 52 is inserted into the discharge port 12 of the container body 10, and the sealing protrusion wheel 54 is tightly closed to an outside of the discharge port 12 of the container body 10, such that the discharge port 12 is sealed.

The descent limiting member 20 is fixedly coupled to the container body 10 while being inserted into the opening hole 14 of the container body 10, thereby controlling the descending distance of the pressing button 30.

As shown in the enlarged view of FIG. 4, a first upper extension protrusion wheel 21 extends upward from the center of the descent limiting member 20. A second upper extension protrusion wheel 22 extends upward while being spaced apart from an outside of the first upper extension protrusion wheel 21 by a predetermined distance. A third upper extension protrusion wheel 23 extends upward while being spaced apart from an outside of the second upper extension protrusion wheel 22 by a predetermined distance.

A piston insertion hole 28 is formed inside the first upper extension protrusion wheel 21 to allow a piston 38 of the pressing button 30 to be inserted into the piston insertion hole 28.

A plurality of main grooves 24 having different depths are formed in the second upper extension protrusion wheel 22. The main groove 24 is formed in the shape of a slit cut vertically to the second upper extension protrusion wheel 22.

The main groove 24 includes first to third main grooves 241 to 243, where the first to third main grooves 241 to 243 are formed to gradually increase in depth.

The first to third main grooves 241 to 243 are formed on the second upper extension protrusion wheel 22 while being separated from each other at a predetermined angle. In the drawings of the present disclosure, the first to third main grooves 241 to 243 are arranged while being spaced apart from each other at 120 degrees, but the present invention is not limited thereto, and the arrangement angle may be variously changed according to the number of main grooves 24.

On the lower inner periphery of the second upper extension protrusion wheel 22, a descent limiting sill 25 is formed to restrict the pressing button 30 from being pressed during keeping or carrying.

A plurality of auxiliary grooves 26 having different depths from each other are formed on the descent limiting sill 25. The auxiliary grooves 26 are formed to face the main grooves 24.

The auxiliary groove 26 includes second and third auxiliary grooves 262 and 263. The second auxiliary groove 262 is paired with the second main groove 242, and the third auxiliary groove 263 is paired with the third main groove 243. The first main groove 241 is paired with the descent limiting sill 25 without being paired with any auxiliary grooves.

Figure 6:
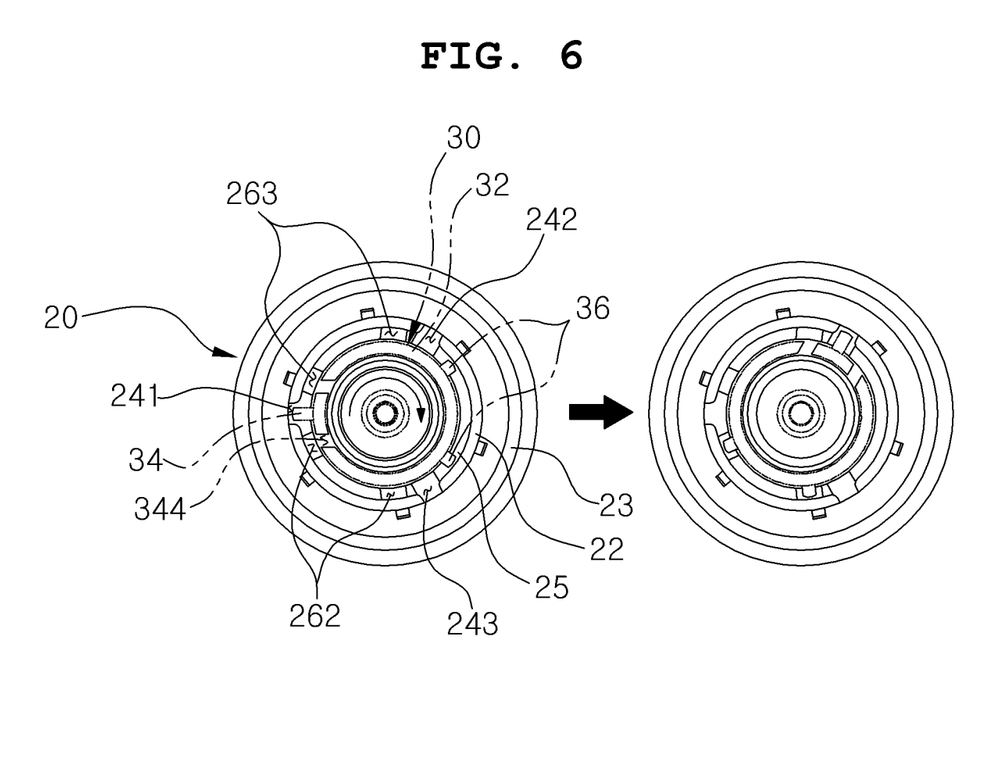
FIG. 6 is a plan view showing a state of rotating the pressing button of the dropping pipette-type cosmetic container according to an embodiment of the present invention.
Figure 8:
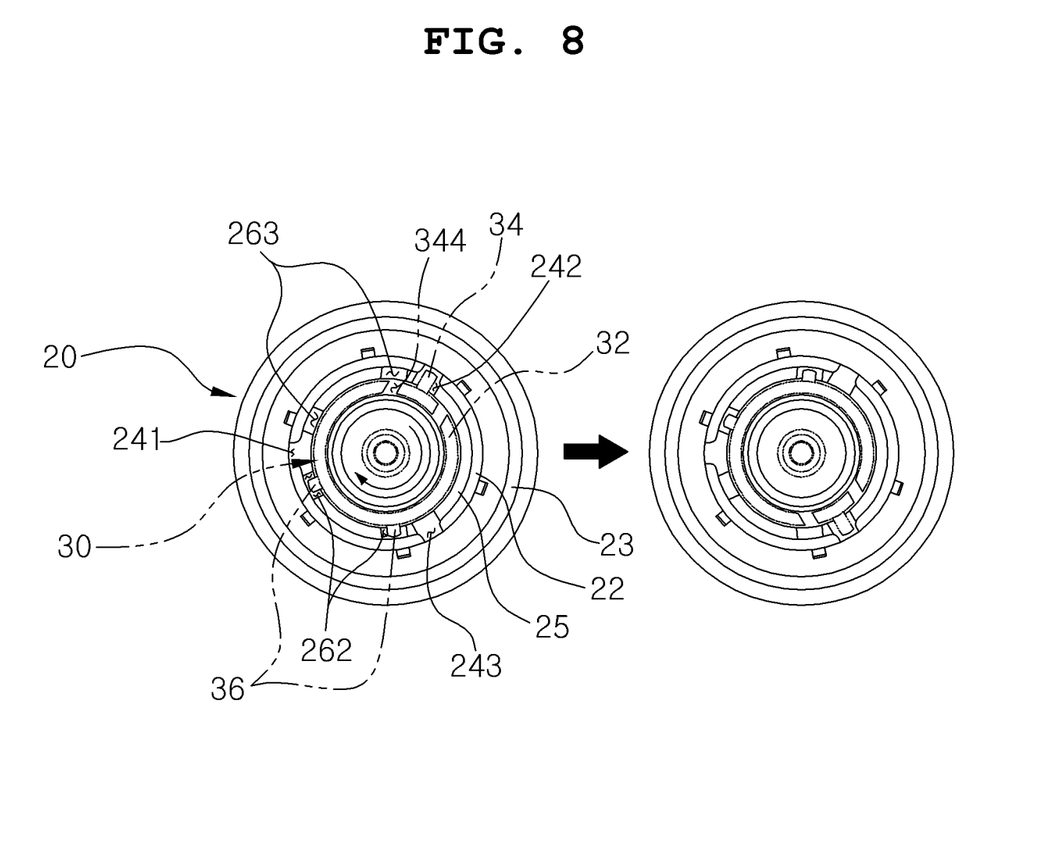
FIG. 8 is a plan view showing a state of further rotating the pressing button of the dropping pipette-type cosmetic container according to an embodiment of the present invention.

That is, when the main protrusion 34 is inserted into the first main groove 241, the auxiliary protrusion 36 is placed on the descent limiting sill 25, such that the pressing button 30 is not pressed. In addition, as shown in FIG. 6, when the main protrusion 34 is inserted into the second main groove 242 by rotating the pressing button 30 at a predetermined angle, the auxiliary protrusion 36 is located in the second auxiliary groove 262. Thus, the main protrusion 34 and the auxiliary protrusion 36 simultaneously move down in the second main groove 242 and the second auxiliary groove 262 by the pressing of the pressing button 30. In addition, as shown in FIG. 8, when the main protrusion 34 is inserted into the third main groove 242 by further rotating the pressing button 30, the auxiliary protrusion 36 is located in the third auxiliary groove 263. Thus, the main protrusion 34 and the auxiliary protrusion 36 simultaneously move down in the third main groove 243 and the third auxiliary groove 263 by the pressing of the pressing button 30.

Accordingly, when the pressing button 30 is pressed, the pressing button 30 does not incline to either side and stably moves down while maintaining a horizontal level, thereby improving convenience of use.

A placing sill 232 is formed on an upper outer periphery of the third upper extension protrusion wheel 23 and is placed on an upper end of the container body 10. A second coupling protrusion wheel 234 protrudes outwardly of the placing sill 232.

The pressing button 30 is rotatably coupled to the descent limiting member 20, and discharges the contents contained in the container body 10 to an outside when pressed by a user.

As shown in the enlarged view of FIG. 4, a first lower extension protrusion wheel 31 extends downward from the center of the pressing button 30. A second lower extension protrusion wheel 32 extends downward while being spaced apart from an outside of the first lower extension protrusion wheel 31 by a predetermined interval. A third lower extension protrusion wheel 33 extends downward while being spaced apart from an outside of the second lower extension protrusion wheel 32 by a predetermined interval.

As shown in FIG. 5, the piston 38 is coupled to a lower portion of the first lower extension protrusion wheel 31. The piston 38 moves up and down while being tightly closed to the inner periphery of the piston insertion hole 28 of the descent limiting member 20.

The second lower extension protrusion wheel 32 is inserted between the first and second upper extension protrusion wheels 21 and 22 of the descent limiting member 20, and the third lower extension protrusion wheel 33 is inserted between the second and third upper extension protrusion wheels 22 and 23 of the descent limiting member 20.

As shown in the enlarged view of FIG. 4, the main protrusion 34 and the auxiliary protrusion 36 protrude outward from the outer periphery of the second lower extension protrusion wheel 32.

The main and auxiliary protrusions 34 and 36 have a vertically long bar shape. The main protrusion 34 moves up and down in the main groove 24 of the descent limiting member 20, and the auxiliary protrusion 36 is inserted into the auxiliary groove 26 of the descent limiting member 20. In this case, the auxiliary groove 26 has the same depth as the main groove 24, and is located opposite the main groove 24.

The main and auxiliary protrusions 34 and 36 protrude from the outside of the second lower extension protrusion wheel 32, As shown in FIGS. 6 and 8, the outer diameter of the main protrusion 34 is formed to be larger than the inner diameter of the second upper extension protrusion wheel 22 on which the main groove 24 is formed. The outer diameter of the auxiliary protrusion 36 is formed to be smaller than the inner diameter of the second upper extension protrusion wheel 22.

Accordingly, the main protrusion 34 is always maintained to be inserted into the main groove 24 of the descent limiting member 20. The auxiliary protrusion 36 is placed on an upper portion of the descent limiting sill 25 formed inside the second upper extension protrusion wheel 22 in a state that the auxiliary protrusion 36 does not contact the inner periphery of the second upper extension protrusion wheel 22 of the descent limiting member 20.

An elastic slit 344 is formed at both sides of the main protrusion 34. As shown in FIG. 4, the elastic slit 344 is formed on the second lower extension protrusion wheel 32 adjacent to the main protrusion 34, and has a shape formed when the second lower extension protrusion wheel 32 is cut vertically.

As described above, the dropping pipette-type cosmetic container according to the present invention is formed on both sides of the main protrusion 34 of the pressing button 30 with the elastic slit 344. When the main protrusion 34 is always inserted into the main groove 24 of the descent limiting member 20 to forcibly rotate the pressing button 30 as shown in FIGS. 6 and 8, the main protrusion 34 of the pressing button 30 retracts elastically by the elastic slit 344, exits the main groove 24, rotates, and is resiliently inserted into another adjacent main groove 24 to prevent the pressing button 30 from being rotated arbitrarily.

Therefore, it is possible to prevent the main protrusion of the pressing button 30 from malfunctioning because the main protrusion is caught in another adjacent portion due to the flowing of the main protrusion 34. In addition, the user may easily recognize through the touch that the lifting distance of the pressing button 30 is adjusted.

The main protrusion 34 and the auxiliary protrusion 36 have the same vertical length, and are positioned opposite to each other based on the first lower extension protrusion wheel 31 of the pressing button 30 as shown in FIG. 4.

A locking portion 332 protrudes outward from a lower portion of the third lower extension protrusion wheel 33, and a locking portion elastic slit 334 is formed at both sides of the locking portion 332 to allow the locking portion 332 to move elastically.

As shown in FIG. 5, when the lowering limit member 20 and the pressing button 30 are coupled to each other, the locking part 332 is hung on the inner lower end of an outer cap 60 so that the pressing button 30 is prevented from being separated from the container body 10.

The elastic member 40 is installed inside the descent limiting member 20 to elastically support the pressing button 30.

As shown in FIG. 5, the elastic member 40 is inserted between the second upper extension protrusion wheel 22 and the third upper extension protrusion wheel 23 of the descent limiting member 20, and the upper end of the elastic member 40 is tightly closed to the lower end of the third lower extension protrusion wheel 33 of the pressing button 30.

In addition, the outer cap 60 is further formed adjacent to the opening hole 14 of the container body 10.

The outer cap 60 is coupled to the outer periphery of the container body 10 while surrounding the upper portion of the container body 10 and the descent limiting member 20, such that the descent limiting member 20 and the pressing button 30 are prevented from being separated from the main body 10.

The outer cap 60 includes an outer wall 61, a horizontal extension piece 62 extending inwardly from an upper portion of the outer wall 61, and a lower extension piece 63 extending downwardly of the horizontal extension piece 62.

Between the outer wall 61 and the lower extension piece 63 of the outer cap 60, an upper portion of the third upper extension protrusion wheel 23 of the lower limiting member 20 is inserted.

The lower extension piece 63 of the outer cap 60 is coupled while surrounding the upper portion of the third upper extension protrusion wheel 23 of the descent limiting member 20, such that the locking portion 332 of the pressing button 30 is locked to the lower end of the lower extension piece 63, thereby preventing the pressing button 30 from being separated from the container body 10.

A first engaging groove 66 is formed on the lower inner periphery of the outer cap 60 to be coupled with the first coupling protrusion wheel 16 of the container body 10, and a second coupling groove 68 is formed on the upper inner periphery to be coupled to the second coupling protrusion wheel 234 of the descent limiting member 20.

Hereinafter, a dropping pipette-type cosmetic container including a pressing button having an adjustable descending distance according to another embodiment of the present invention will be described in detail with reference to the accompanying drawings.

Figure 10:
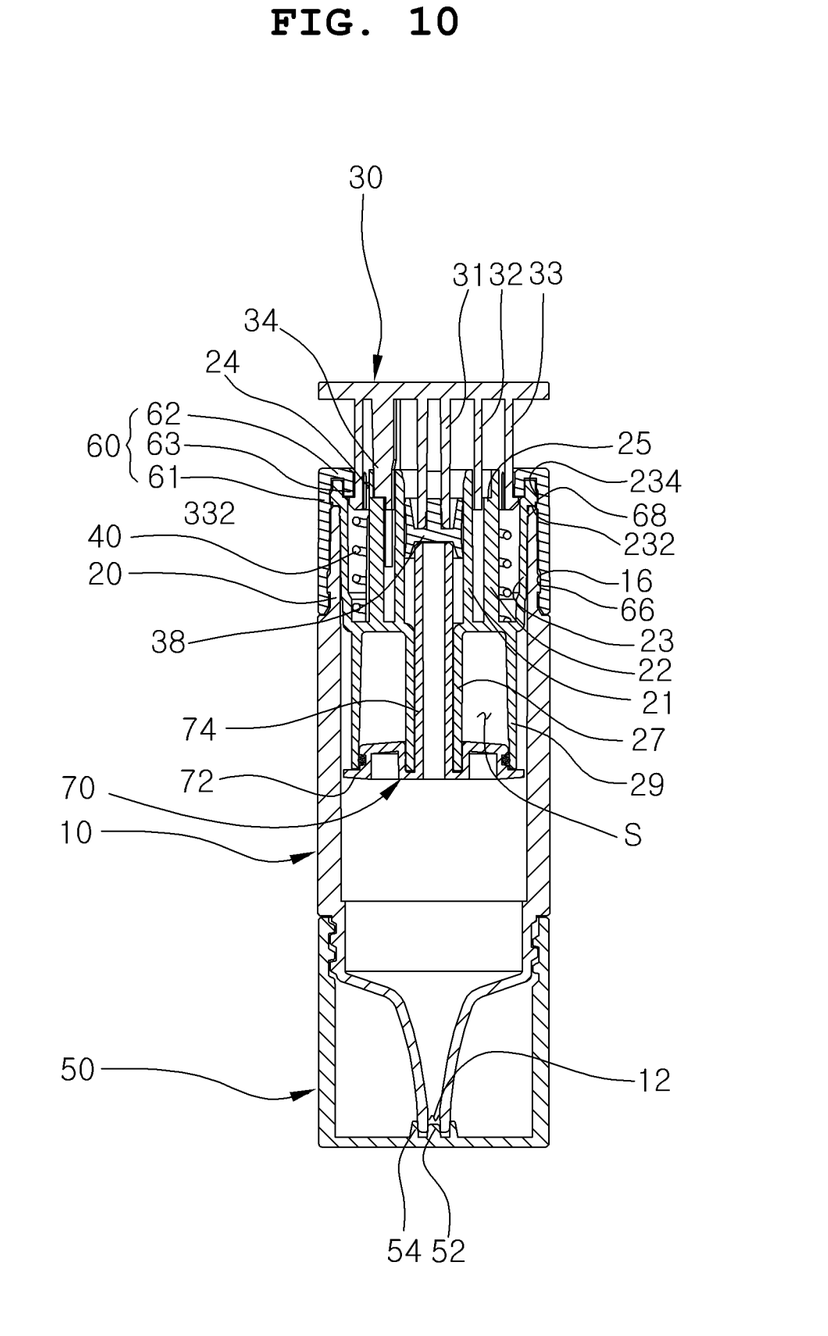
FIG. 10 is a cross-sectional view of a dropping pipette-type cosmetic container according to another embodiment of the present invention.
Figure 11:
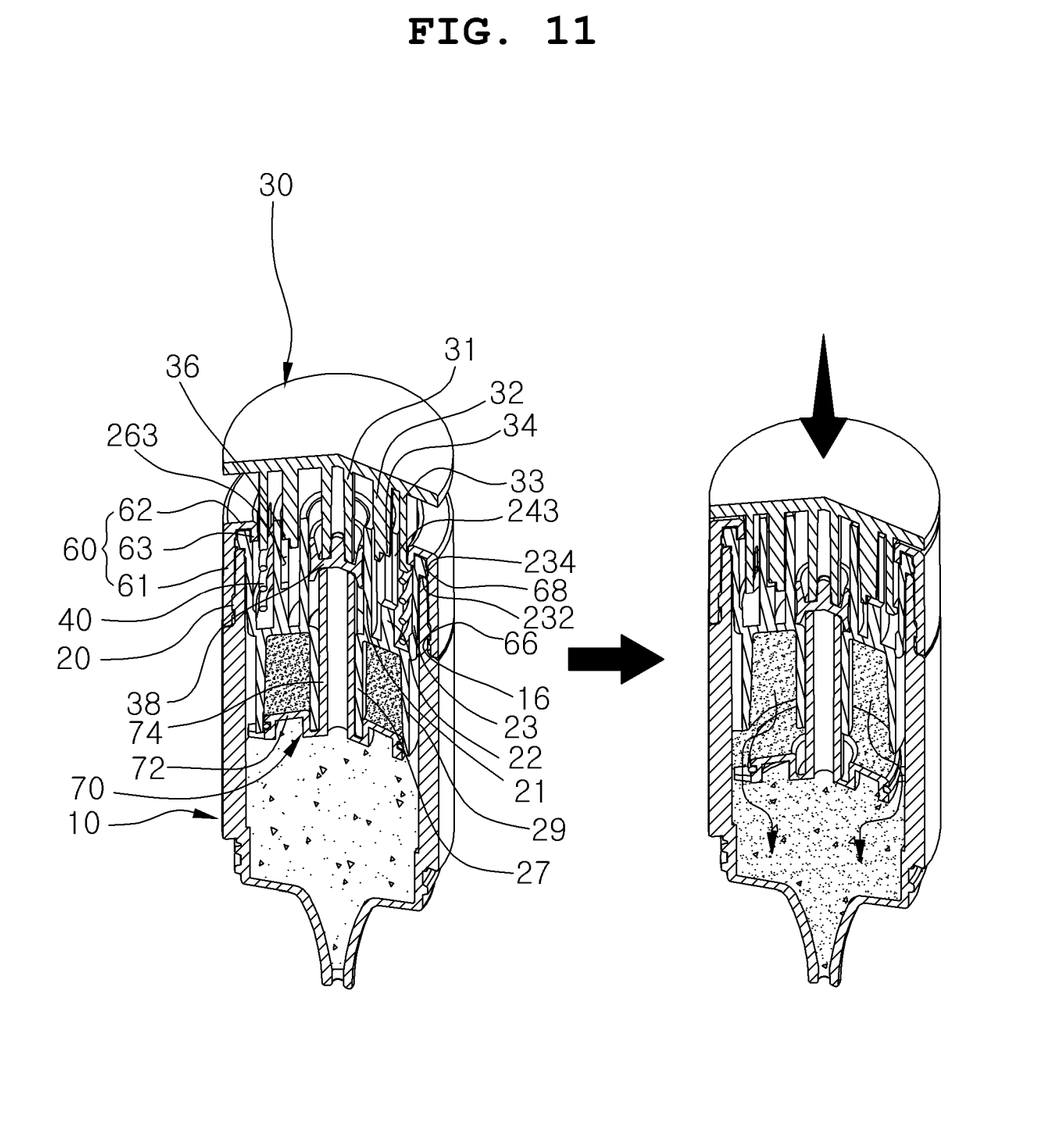
FIG. 11 is a partial cross-sectional view showing a state in which heterogeneous contents are mixed by pressing a pressing button of a dropping pipette-type cosmetic container according to another embodiment of the present invention.

FIG. 10 is a cross-sectional view of a dropping pipette-type cosmetic container according to another embodiment of the present invention. FIG. 11 is a partial cross-sectional view showing a state in which heterogeneous contents are mixed by pressing a pressing button of a dropping pipette-type cosmetic container according to another embodiment of the present invention.

The dropping pipette-type cosmetic container according to another embodiment of the present invention may separately contain heterogeneous contents in the container body 10 and the descent limiting member 20, and then mixed with the heterogeneous contents in the first use. Because the content discharging structure and the descending distance adjusting structure of the pressing button of the dropping pipette-type cosmetic container according to another embodiment of the present invention are the same as the dropping pipette-type cosmetic container according to an embodiment of the present invention described above, the detailed description will be omitted.

As shown in FIG. 10, an inner wall 27 extends to the lower center of the descent limiting member 20, and an outer wall 29 extends to the lower side while being spaced apart from the outside of the inner wall by a predetermined interval.

Between the inner and outer walls 27 and 29 of the descent limiting member 20, a heterogeneous content containing space S is formed to contain contents different from those contained in the container body 10.

A heterogeneous content closing member 70 for closing the heterogeneous content containing space S is coupled to the lower portion of the descent limiting member 20.

The heterogeneous contents closing member 70 includes a closing part 72 coupled to the lower end of the descent limiting member 20, and a pressing part 74 extending upwardly toward the center of the closing part 72.

The closing part 72 is coupled to the lower portions of the inner and outer walls 27 and 29 of the descent limiting member 20 to block the heterogeneous content containing space S.

The pressing part 74 is inserted into the piston insertion hole 28 of the descent limiting member 20 to be tightly closed to the lower portion of the piston 38 of the pressing button 30.

As shown in FIG. 11, when the pressing button 30 is first pressed, the piston 38 coupled to the lower center of the pressing button 30 presses the pressing part 74 of the heterogeneous content closing member 70 while moving downward. At the same time, as the heterogeneous content closing member 70 moves downward, the closing part 72 of the heterogeneous content closing member 70 is separated from the descent limiting member 20.

Accordingly, as the heterogeneous content containing space S is opened, the contents contained in the heterogeneous content containing space S flow out into the container body 10 and are mixed with the contents contained in the container body 10.

Hereinafter, a method of assembling the dropping pipette-type cosmetic container including a pressing button having an adjustable descending distance described above will be described.

In order to assemble the dropping pipette-type cosmetic container including a pressing button having an adjustable descending distance according to the present invention, as shown in FIGS. 4 and 5, the container cover 50 is coupled to one side of the container body 10. The sealing protrusion 52 of the container cover 50 is inserted into the discharge port 12 of the container body 10, and the sealing protrusion 54 is tightly closed to the outside of the discharge port 12 of the container body 10 to block the discharge port 12.

Next, after the container body 10 is turned over, the contents are filled through the opening hole 14 of the container body 10.

Next, while the descent limiting member 20 is inserted into the opening hole 14 of the container body 10 from the top, the placing sill 232 of the descent limiting member 20 is placed on the upper end of the container body 10.

In this case, when the heterogeneous content closing member 70 is further coupled to the descent limiting member 20, first, the heterogeneous content containing space S formed between the inner and outer walls 27 and 29 of the descent limiting member 20 is filled with heterogeneous contents. While the pressing part 74 of the heterogeneous content closing member 70 is inserted into the piston insertion hole 28 of the descent limit member 20, the closing part 72 of the heterogeneous content closing member 70 is coupled to the inner and outer walls 27 and 29 of the descent limiting member 20 to block the heterogeneous content containing space S, and then, the descent limiting member 20 is inserted into the opening hole 14 of the container body 10 from the top.

Next, the outer cap 60 is coupled to the upper portion of the container body 10. While the outer cap 60 covers a portion of the container body 10 and the upper portion of the descent limiting member 20, the first coupling protrusion wheel 16 of the container body 10 is coupled into the first coupling groove 66 of the outer cap 60, and the second coupling protrusion wheel 234 of the descent limiting member 20 is coupled into the second coupling groove 68, such that the lower limiting member 20 is fixed to the container body 10.

Next, the elastic member 40 is inserted between the second and third upper extension protrusion wheels 22 and 23 of the descent limiting member 20.

Next, the piston 38 is fixedly coupled to the lower portion of the first lower extension protrusion wheel 31 of the pressing button 30, and the pressing button 30 is fitted to the upper portion of the descent limiting member 20. The piston 38 of the pressing button 30 is inserted into the piston insertion hole 28 of the descent limiting member 20, and the second low extension protrusion wheel 32 of the pressing button 30 is inserted between the first and second upper extension protrusion wheels 21 and 22 of the descent limiting member 20. The third low extension protrusion wheel 33 of the pressing button 30 is inserted between the second and third upper extension protrusion wheels 22 and 23 of the descent limiting member 20.

As described above, when the pressing button 30 is fitted to the upper portion of the descent limiting member 20, while the locking portion 332 protruding outward of the pressing button 30 is elastically pushed inward by the locking portion elastic slit 334, the locking portion 332 moves over the lower extension piece 63 of the outer cap 60 to be locked to the lower end of the lower extension piece 63. Accordingly, it is possible to prevent the pressing button 30 from being separated from the container body 10.

Hereinafter, a method of using the dropping pipette-type cosmetic container including a pressing button having an adjustable descending distance assembled as described above will be described.

Figure 7:
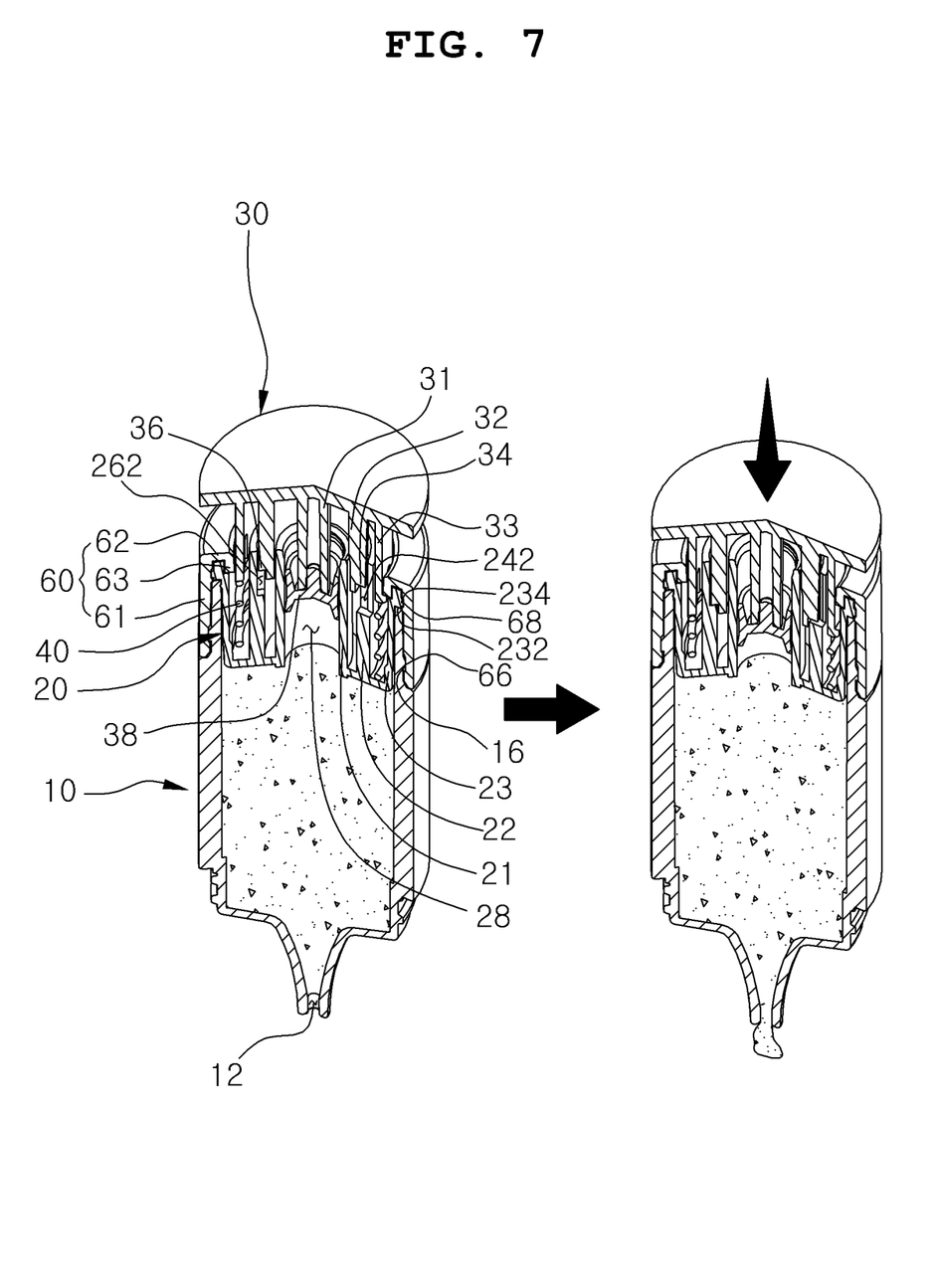
FIG. 7 is a partial cross-sectional view showing a state in which the contents are discharged by pressing the pressing button of the dropping pipette-type cosmetic container according to an embodiment of the present invention.
Figure 9:
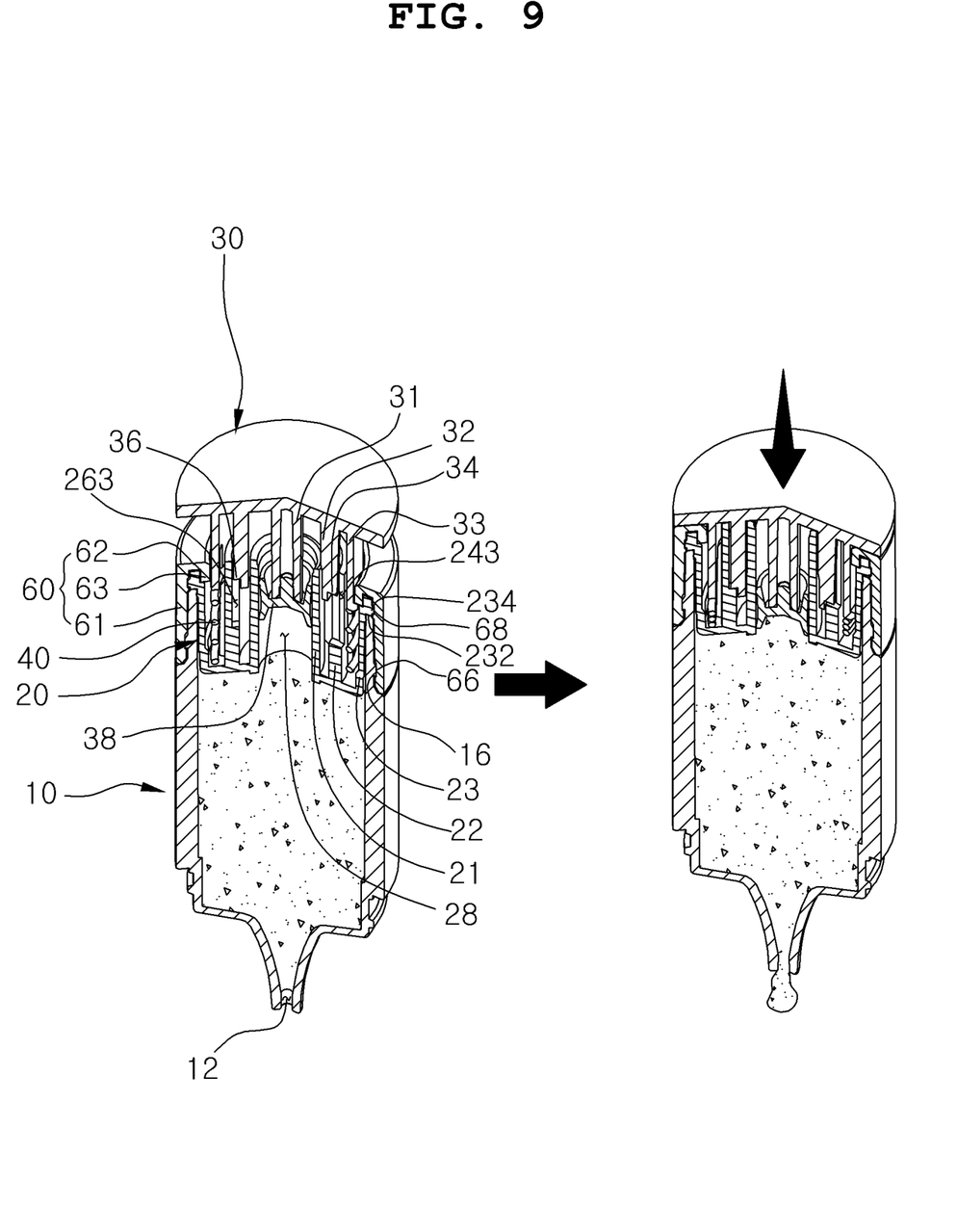
FIG. 9 is a partial cross-sectional view showing a state in which a larger amount of contents is discharged by pressing the pressing button of the dropping pipette-type cosmetic container according to an embodiment of the present invention.

FIG. 6 is a plan view showing a state of rotating the pressing button of the dropping pipette-type cosmetic container according to an embodiment of the present invention. FIG. 7 is a partial cross-sectional view showing a state in which the contents are discharged by pressing the pressing button of the dropping pipette-type cosmetic container according to an embodiment of the present invention. FIG. 8 is a plan view showing a state of further rotating the pressing button of the dropping pipette-type cosmetic container according to an embodiment of the present invention. FIG. 9 is a partial cross-sectional view showing a state in which a larger amount of contents is discharged by pressing the pressing button of the dropping pipette-type cosmetic container according to an embodiment of the present invention.

In order to use the dropping pipette-type cosmetic container including a pressing button having an adjustable descending distance according to the present invention, as shown in FIG. 3, the container cover 50 is separated from the container body 10 to open the discharge port 12.

First, the method of use in the case of discharging a relatively small amount of contents to use is as follows.

As shown in the left view of FIG. 6, the main protrusion 34 of the pressing button 30 is inserted into the first main groove 241 of the descent limiting member 20. The auxiliary protrusion 36 of the pressing button 30 is placed on the upper end of the descent limiting sill 25 of the descent limiting member 20, so that the pressing button 30 is not pressed.

Thereafter, when the pressing button 30 is forcibly rotated, the main protrusion 34 of the pressing button 30 is retracted elastically by the elastic slit 344 and exits the first main groove 241. When the pressing button 30 is continuously rotated, the main protrusion 34 of the pressing button 30 is rotated in close contact with the inner periphery of the second upper extension protrusion wheel 22 of the descent limiting member 20, and then, is elastically inserted into the second main groove 242 as shown in the right view of FIG. 6. In this case, the auxiliary protrusion 36 of the pressing button 30 is located on the upper portion of the second auxiliary groove 262.

Thereafter, as shown in FIG. 7, when the pressing button 30 is pressed, the main protrusion 34 and the auxiliary protrusion 36 of the pressing button 30 move down due to the depth of the second main groove 242 and the second auxiliary groove 262 in the second main groove 242 and the second auxiliary groove 262. At the same time, as the piston 38 coupled to the lower portion of the pressing button 30 descends in close contact with the inner periphery of the piston insertion hole 28 of the descent limiting member 20, the inner volume of the container body 10 is reduced by the length at which the piston 38 descends, so that a relatively small amount of contents is discharged to the outside through the discharge port 12.

Next, the method of use in the case of discharging a relatively large amount of contents to use is as follows.

As shown in the left view of FIG. 8, when the pressing button 30 is further rotated forcibly, the main protrusion 34 of the pressing button 30 inserted into the second main groove 242 of the descent limiting member 20 is resiliently retracted by the elastic slit 344, so that the second main groove 242 exits. When the pressing button 30 is continuously rotated, the main protrusion 34 of the pressing button 30 is rotated in close contact with the inner periphery of the second upper extension protrusion wheel 22 of the descent limiting member 20, and then, as shown in the right view of FIG. 8, the main protrusion 34 is elastically inserted into the third main groove 243 formed deeper than the second main groove 242.

In this case, the auxiliary protrusion 36 of the pressing button 30 located at the upper portion of the second auxiliary groove 262 of the descent limiting member 20 is located at the upper portion of the third auxiliary groove 263.

Thereafter, as shown in FIG. 9, when the pressing button 30 is pressed, the main protrusion 34 and the auxiliary protrusion 36 of the pressing button 30 move down in the third main groove 243 and the third auxiliary groove 263 due to the depths of the third main groove 243 and the third auxiliary groove 263. At the same time, as the piston 38 coupled to the lower portion of the pressing button 30 moves down in close contact with the inner periphery of the piston insertion hole 28 of the descent limiting member 20, while the inner volume of the container body 10 is reduced by the descending distance of the piston 38, so that a relatively large amount of contents is discharged to an outside through the discharge port 12.

In addition, in order to prevent the pressing button 30 from being arbitrarily pressed during keeping or carrying, the pressing button 30 is rotated in the opposite direction.

When the pressing button 30 is rotated in the opposite direction, the main protrusion 34 of the pressing button 30 inserted into the second or third main groove 242 or 243 of the descent limiting member 20 is resiliently retracted by the elastic slit 344, so that the second or third main groove 242 or 243 exits. When the pressing button 30 is continuously rotated in the opposite direction, the main protrusion 34 of the pressing button 30 is rotated in close contact with the inner periphery of the second upper extension protrusion wheel 22 of the descent limiting member 20, so that the main protrusion 34 is elastically inserted into the first main groove 241. In this case, the auxiliary protrusion 36 of the pressing button 30 is placed on the upper end of the descent limiting sill 25.

As described above, the auxiliary protrusion 36 of the pressing button 30 is locked to the descent limiting sill 25 of the descent limiting member 20 so that the pressing button 30 is not pressed.

Thereafter, the container cover 50 is again coupled to the container body 10 to be kept with the discharge port 10 closed.

As described above, the dropping pipette-type cosmetic container including a pressing button having an adjustable descending distance described in this disclosure is an illustrative purpose only, and the present invention is not limited thereto. Thus, it should be understood that numerous other modifications and embodiments can be devised by those skilled in the art within the spirit and scope of the present invention and they will fall within the scope of the present invention.

What is claimed is:

1. A dropping pipette-type cosmetic container including a pressing button having an adjustable descending distance, the dropping pipette-type cosmetic container comprising:
    a container body having a discharge port formed on one side thereof;
    a descent limiting member fixedly coupled to an opposite side of the container body, formed with a plurality of main grooves having different depths, and formed with a plurality of auxiliary grooves, which have a same depth as each of the plurality of main grooves and are formed on a descent limiting sill;
    a pressing button rotatably coupled to the descent limiting member and having a main protrusion inserted into the main groove and an auxiliary protrusion inserted into the auxiliary groove; and
    an elastic member for elastically supporting the pressing button,
    wherein, when the pressing button is rotated at a predetermined angle, the main protrusion of the pressing button is inserted into one of the plurality of main grooves of the descent limiting member while the auxiliary protrusion is located on the auxiliary groove or the descent limiting sill.

2. The dropping pipette-type cosmetic container of claim 1, further comprising a container cover coupled to one side of the container body to open and close a discharge port of the container body.

3. The dropping pipette-type cosmetic container of claim 1, further comprising an outer cap coupled to an opposite side of the container body to surround the container body and the descent limiting member.

4. The dropping pipette-type cosmetic container of claim 1, wherein the descent limiting member is formed with a piston insertion hole, and the pressing button is formed with a piston inserted into the piston insertion hole.

5. The dropping pipette-type cosmetic container of claim 1, wherein the main groove of the descent limiting member includes first to third main grooves having depths different from each other, and the auxiliary groove includes a second auxiliary groove mating with the second main groove and a third auxiliary groove mating with the third main groove.

6. The dropping pipette-type cosmetic container of claim 5, wherein the depth gradually increases from the first main groove to the second main groove and the third main groove.

7. The dropping pipette-type cosmetic container of claim 1, further comprising elastic slits formed on two sides of the main protrusion of the pressing button, wherein the main protrusion protrudes outward and is kept in an insertion state into the main groove of the descent limiting member such that the main protrusion is elastically inserted into and released from the main groove.

8. The dropping pipette-type cosmetic container of claim 7, wherein an outer diameter of the main protrusion is larger than an inner diameter of a second upper extension protrusion wheel in which the main groove is formed, and an outer diameter of the auxiliary protrusion is smaller than the inner diameter of the second upper extension protrusion wheel.

9. The dropping pipette-type cosmetic container of claim 1, wherein a heterogeneous content containing space is formed at one side of the descent limiting member to contain a content different from a content contained in the container body, and a heterogeneous content closing part for closing the heterogeneous content containing space is coupled to the descent limiting member.

10. The dropping pipette-type cosmetic container of claim 9, wherein the heterogeneous content closing part is separated from the descent limiting member while being moved by pressing of the pressing button, such that the heterogeneous content containing space is opened to mix heterogeneous contents.

* * * * *